United States Patent
Oh et al.

(10) Patent No.: US 6,771,418 B2
(45) Date of Patent: Aug. 3, 2004

(54) METHOD AND APPARATUS FOR EXTRACTING THREE-DIMENSIONAL SPACIAL DATA OF OBJECT USING ELECTRON MICROSCOPE

(75) Inventors: Chil Hwan Oh, Seoul (KR); Jong Sub Moon, Seoul (KR); Min Gi Kim, Seoul (KR)

(73) Assignee: Korea Chungang Educational Foundation, Seoul (KR)

( * ) Notice: Subject to any disclaimer, the term of this patent is extended or adjusted under 35 U.S.C. 154(b) by 0 days.

(21) Appl. No.: 10/462,596

(22) Filed: Jun. 17, 2003

(65) Prior Publication Data

US 2004/0026619 A1 Feb. 12, 2004

(30) Foreign Application Priority Data

Aug. 9, 2002 (KR) ........................................ 2002-47200

(51) Int. Cl.[7] ........................ G02B 21/00; G02B 21/36; G02B 27/64
(52) U.S. Cl. .................... 359/368; 359/385; 250/201.3; 250/310; 250/311; 702/152
(58) Field of Search .............................. 250/201.3, 310, 250/311, 458.1; 356/72; 359/368, 370, 383, 385; 438/700, 637; 702/159, 166, 152

(56) References Cited

U.S. PATENT DOCUMENTS

| | | | | |
|---|---|---|---|---|
| 5,563,962 A | * | 10/1996 | Peters et al. ................. | 382/261 |
| 5,715,334 A | * | 2/1998 | Peters ......................... | 382/254 |
| 6,098,031 A | * | 8/2000 | Svetkoff et al. ............. | 702/159 |
| 6,505,140 B1 | * | 1/2003 | Bachrach ..................... | 702/166 |
| 6,593,231 B2 | * | 7/2003 | Endoh et al. ................ | 438/637 |
| RE38,307 E | * | 11/2003 | Gustafsson et al. ......... | 359/385 |
| 2002/0137350 A1 | * | 9/2002 | Endoh et al. ................ | 438/700 |

* cited by examiner

Primary Examiner—Nikita Wells
Assistant Examiner—Mary El-Shammaa
(74) Attorney, Agent, or Firm—Rothwell, Figg, Ernst & Manbeck, p.c.

(57) ABSTRACT

A method and apparatus for extracting three-dimensional data of an object using an electron microscope are provided. The method for extracting the three-dimensional data of the object includes: obtaining two-dimensional coordinates by respectively projecting the object on a plane perpendicular to an X-axis, on a plane perpendicular to a Y-axis, and on a plane making an angle of 45 degrees from a Z-axis with a Y-Z plane; in portions where three images including the two-dimensional coordinates overlapped, obtaining data of a pixel on a base images among the three images, obtaining data of corresponding pixels of the pixel on the base image to left and right images of the base image, and calculating a disparity on the basis of the data; and extracting three-dimensional depth information of the object using the obtained disparity, the three-dimensional depth information representing a relative distance of the object, and extracting a three-dimensional coordinate on each pixel to determine a three-dimensional location of the object.

15 Claims, 4 Drawing Sheets

PLANE PERPENDICULAR
TO X-AXIS

PLANE PERPENDICULAR
TO Y-AXIS

PLANE AT 45 DEGREES
FROM Z-AXIS WITH
RESPECT TO THE Y-Z PLANE

METHOD AND APPARATUS FOR EXTRACTING THREE-DIMENSIONAL SPACIAL DATA OF OBJECT USING ELECTRON MICROSCOPE

BACKGROUND OF THE INVENTION

This application claims priority from Korean Patent Application No. 2002-47200, filed on Aug. 9, 2002, in the Korean Intellectual Property Office, the disclosure of which is incorporated herein in its entirety by reference.

1. Field of the Invention

The present invention relates to a method for measuring states of an object, and more particularly, to a method and apparatus for extracting three-dimensional data of an object using an electron microscope.

2. Description of the Related Art

Electron microscopes, particularly, scanning electron microscopes (hereinafter, referred to as 'SEM') are apparatuses which have been utilized in various technical fields including the semiconductor industries, medical science, biology, etc. The scanning electron microscopes frequently are required over various industry fields, but most SEM equipments have many problems due to their complicated operation methods and difficult maintenance and repair work. Therefore, the utilization rate of the SEM equipments is very low.

In particular, SEMs capable of measuring an object while directly observing a two-dimensional structure of the object are widely used. In this case, raw data acquired with an SEM is then converted into three-dimensional data, and general surface quantification parameters are two-dimensional data. However, in many situations, it is necessary to perform a three-dimensional measure of objects by quantifying various types of three-dimensional parameters with three-dimensional data in order to three-dimensionally observe the objects. As such, it may be possible to measure lengths, diameters, and angles of structures on cell surfaces, sizes and distances of organellas, etc. However, such SEM equipment has not yet been developed.

In images observed by a conventional SEM, it is possible to determine the interrelation of the structures qualitatively. The conventional SEM processes the images analogically and uses only information from a one-axis when obtaining images for analysis. Accordingly, it is difficult to obtain a precise measuring result. In addition, it is practically impossible to measure three-dimensional structures using the conventional SEM. For this reason, there is a need for a method and apparatus for measuring a three-dimensional structure using an electron microscope, so that the interrelation of structures can be analyzed quantitatively through images converted to three-dimensional data.

SUMMARY OF THE INVENTION

The present invention provides a method and apparatus for extracting three-dimensional data of an object, using an electron microscope which processes images digitally, differently from conventional SEMs, and measures a three-dimensional structure using information obtained from three-axis directions, differently from conventional methods which create images using only information obtained from an one-axis direction.

According to an aspect of the present invention, there is provided a method for extracting three-dimensional data of an object using an electron microscope, the method comprising: obtaining two-dimensional coordinates by respectively projecting the object on a plane perpendicular to an X-axis, on a plane perpendicular to a Y-axis, and on a plane making an angle of 45 degrees from a Z-axis with a Y-Z plane, in an XYZ coordinate system; in portions where three images including the two-dimensional coordinates overlapped, obtaining data of a pixel on a base images among the three images, obtaining data of corresponding pixels of the pixel on the base image to left and right images of the base image, and calculating a disparity on the basis of the data; and extracting three-dimensional depth information of the object using the obtained disparity, the three-dimensional depth information representing a relative distance of the object, and extracting a three-dimensional coordinate on each pixel to determine a three-dimensional location of the object.

According to another aspect of the present invention, there is provided an apparatus for extracting three-dimensional data of an object using an electron microscope, the apparatus comprising: sensors which sense two-dimensional coordinates obtained by respectively projecting the object respectively on a plane perpendicular to an X-axis, a plane perpendicular to a Y-axis, and a plane making an angle of 45 degrees from a Z-axis with a Y-Z plane; a disparity determination unit which, in respective overlapped portions of three images including the two-dimensional coordinates respectively sensed by the sensors, obtains data of corresponding pixels of a pixel on a base image to left and right images of the base image, and calculates a disparity on the basis of the data; and three-dimensional data extraction unit which extracts three-dimensional depth information of the object using the disparity determined by the disparity determination unit, the three-dimensional depth information representing a relative distance of the object, and extracts a three-dimensional coordinate on each pixel to determine a three-dimensional location of the object.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, embodiments of the present inventions will be described in detail with reference to the appended drawings.

Figure 1:
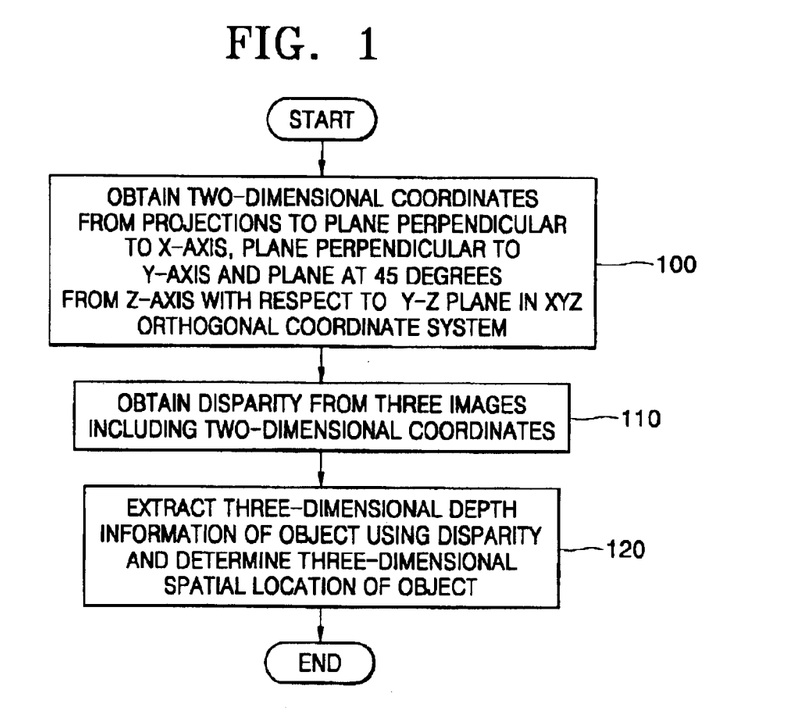
FIG. 1 is a flow chart illustrating a method for extracting three-dimensional data of an object using an electron microscope according to the present invention.

FIG. 1 is a flow chart illustrating a method for extracting three-dimensional data of an object using an electron microscope, according to the present invention.

First, two-dimensional coordinates are sensed by respectively projecting the object on a plane perpendicular to an X-axis, on a plane perpendicular to a Y-axis, and on a plane making an angle of 45 degrees from a Z-axis with a Y-Z plane, in an XYZ coordinate system (step 100). In portions where three images including the two-dimensional coordinates overlapped, data of a pixel on a base images among the three images is obtained, data of corresponding pixels of the pixel on the base image to left and right images of the base image is obtained, and a disparity is calculated on the basis of the data (step 110). Three-dimensional depth information of the object is obtained using the obtained disparity, wherein the three-dimensional depth information represents a relative distance of the object, and a three-dimensional coordinate on each pixel is obtained to determine a three-dimensional location of the object (step 120).

Figure 2:
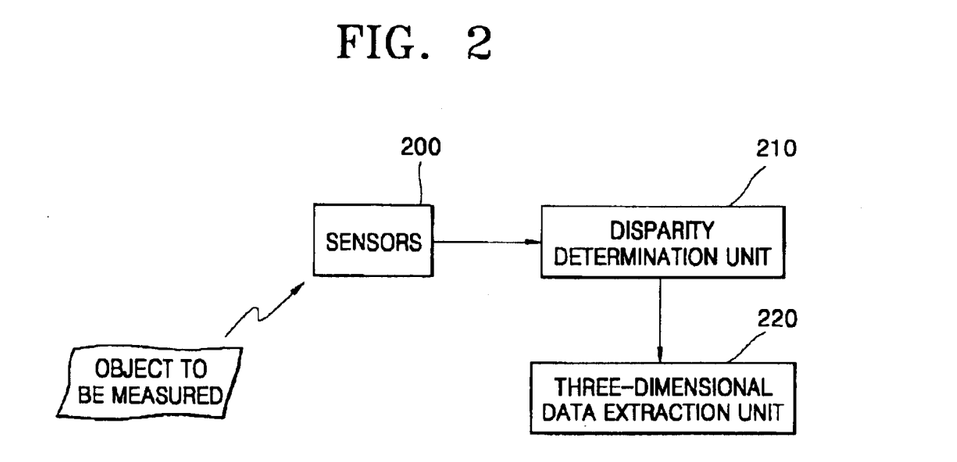
FIG. 2 is a block diagram schematically showing a structure of an apparatus for extracting three-dimensional data of an object using an electron microscope according to the present invention.

FIG. 2 is a block diagram schematically showing the structure of an apparatus for extracting three-dimensional data of the object using the electron microscope, according to the present invention.

This apparatus comprises: sensors which sense two-dimensional coordinates obtained by respectively projecting the object respectively on a plane perpendicular to an X-axis, a plane perpendicular to a Y-axis, and a plane making an angle of 45 degrees from a Z-axis with a Y-Z plane; a disparity determination unit which, in respective overlapped portions of three images including the two-dimensional coordinates respectively sensed by the sensors, obtains data of corresponding pixels of a pixel on a base image to left and right images of the base image, and calculates a disparity on the basis of the data; and three-dimensional data extraction unit which extracts three-dimensional depth information of the object using the disparity determined by the disparity determination unit, the three-dimensional depth information representing a relative distance of the object, and extracts a three-dimensional coordinate on each pixel to determine a three-dimensional location of the object.

Data respectively acquired by three sensors with respect to a plane perpendicular to an X-axis, a plane perpendicular to a Y-axis, and a plane at 45 degrees from the Z-axis relative to a Y-Z plane. Three-dimensional data of an object is extracted using these values. If one point in space is denoted as a point (X,Y,Z), a spatial location of this point is projected on the above-mentioned planes.

The inventor of the present invention has developed a stereo matching technique for extracting three-dimensional data and three-dimensional parameter suited to measure skin surface. Details of this research are presented in:

"Evaluation of Skin furrows in Aging Process using Stereo Image," by Chil-Hwan Oh, Min-Gi Kim, and Jong-Seop Moon, research report, the Korean Ministry of Health-Welfare, 1998.

"Evaluation of Skin furrows in Aging Process using Stereo Image," by Chil-Hwan Oh, Min-Gi Kim, and Jong-Seop Moon, Skin Research and Technology, 1997,3(3),202.

The disclosure of the present invention is related to the technique reported in the above papers.

In extracting three-dimensional data, the stereo matching technique uses the following methods.

1. Extraction of characteristics: extracting characteristics by applying a Zero Mean Normalized Cross Covariance (ZNCC) method to the left and right images of an object Covariance value of brightness values of pixels included in a predetermined window size centering at a given point is used as a similarity standard. That is, the covariance value is obtained by averaging and dispersing the brightness values of the pixels included in the window at each node as seen in Equation 1 below. Details on this can be found in the paper "Repeatedly Relaxed Matching Algorithm using Matching Coincidence," by W. G. Lee, Y. S. Kim, K. H. Do, and Y. H. Ha, Journal of The Institute of Electronics Engineering of Korea (IEEK), Vol.33, chapter B., No.1, 1995.

$$P'_{k,j,d} = \frac{\sum (g_L(k, i) - \mu_L)(g_R(k, i+d) - \mu_R)}{\sqrt{\sum (g_L(k, i) - \mu_L)^2 \sum (g_R(k, i+d) - \mu_R)^2}} \quad (1)$$

Here, $\mu_L$ and $\mu_R$ are average values of the brightness values of the pixels included in the correlation window of the left and right images, respectively.

2. Matching the left and right images

Figure 3:
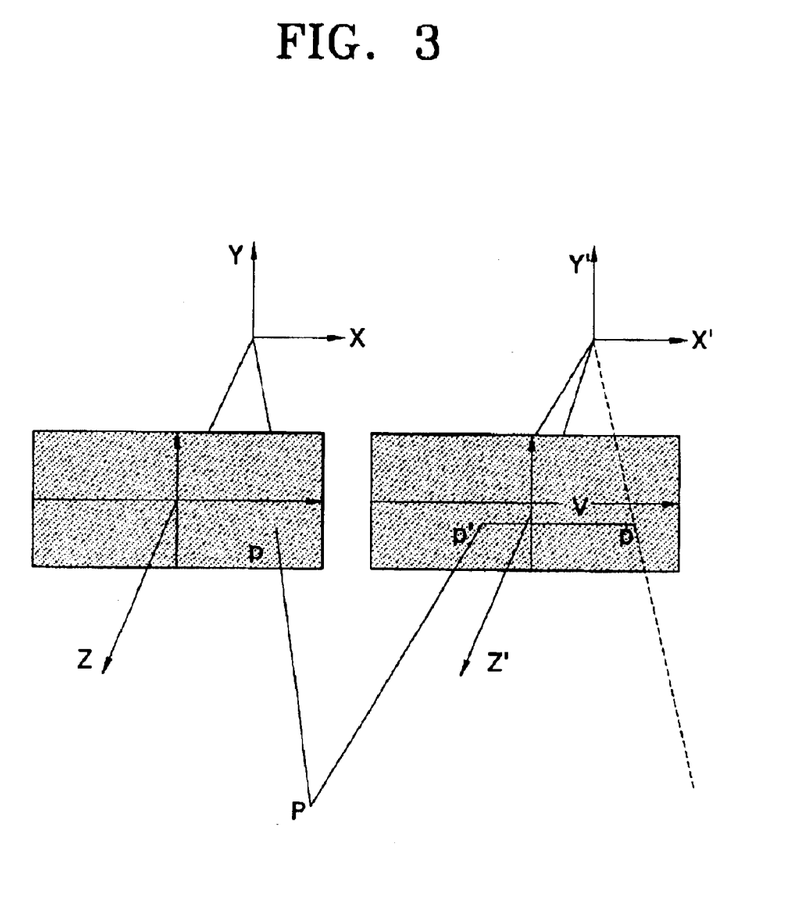
FIG. 3 is a view in which a point in a three-dimensional space is projected respectively to different locations on left and right images of the electron microscope.

As shown in FIG. 3, one point in a three-dimensional space is projected to different locations on the left and right images. The location of a point p' in the right image corresponds to the horizontally shifted location of a point p in the left image by the size v. Points p' and p are located on same horizontal line called the epipolar line. That is, the epipolar line is a line connecting the two points in the left and right images. FIG. 3 shows the left and right images of an object P (the stereo image of the object).

Referring to FIG. 3, the distance on the horizontal line (v) between the points p and p' is called disparity. In perspective projections, the depths of these two points may be recovered using the disparity value. In the following description, it is assumed that an area in the image on which the surface of the object is projected has a predetermined size of w.

Now, the extraction of the three-dimensional coordinates using the electron microscope will be described according to the present invention.

Figure 4:
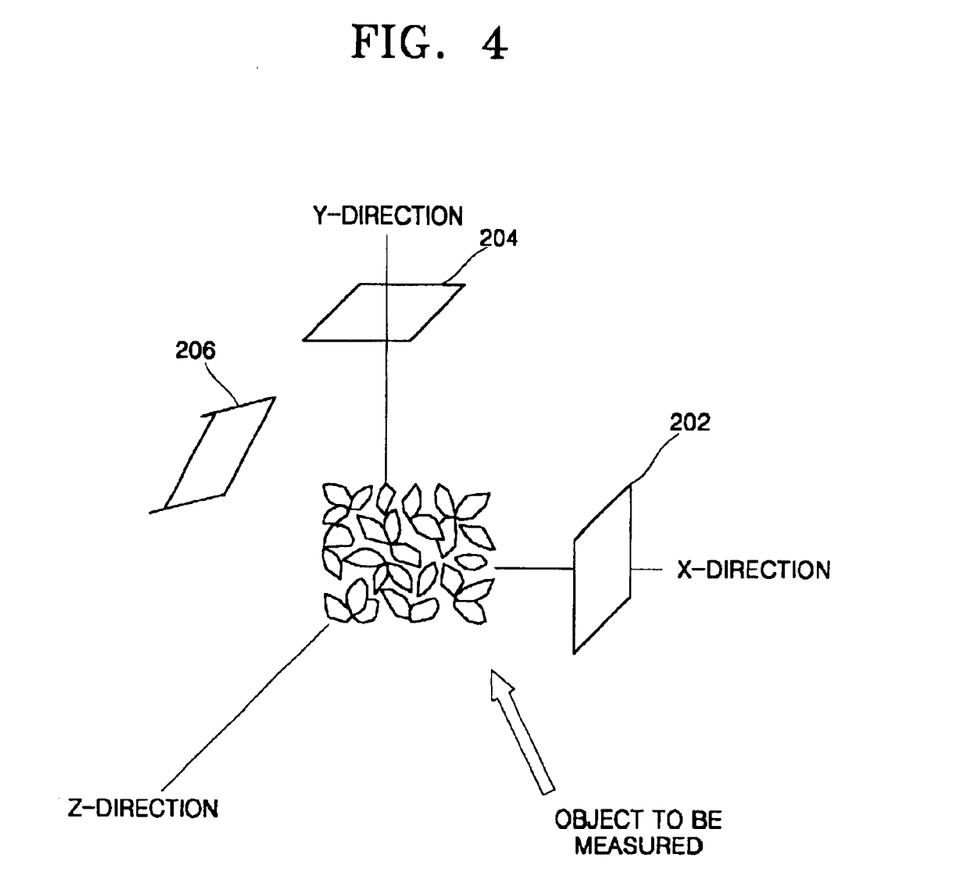
FIG. 4 shows locations of three sensors according to the present invention.

FIG. 4 shows locations of three sensors 202, 204 and 206 according to the present invention. Referring to FIG. 1 and FIG. 4, first, object data are acquired using the sensors 202, 204 and 206 located inside the electrode microscope (step 100). The sensors include a sensor 202 on an X-axis direction, a sensor 204 on a Y-axis direction, and a sensor placed at angle of 45 degrees from a Z-axis with respect to a Y-Z plane.

Figure 5:
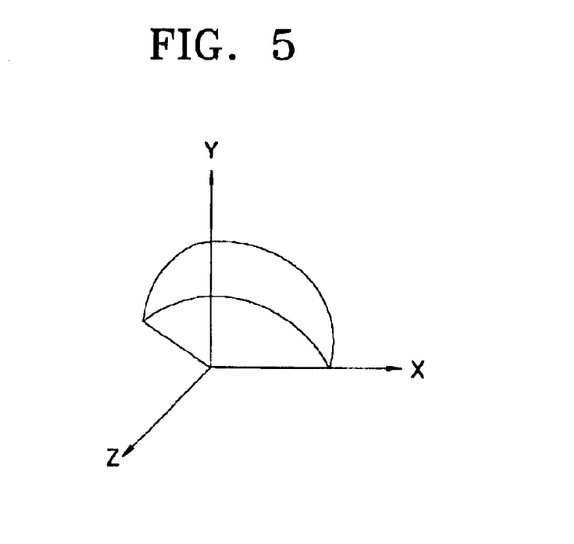
FIG. 5 shows ⅛ of a hemisphere wherein data acquired using the three sensors overlap, according to the present invention.

Data acquired using the sensors overlap as shown in FIG. 5.

Figure 6:
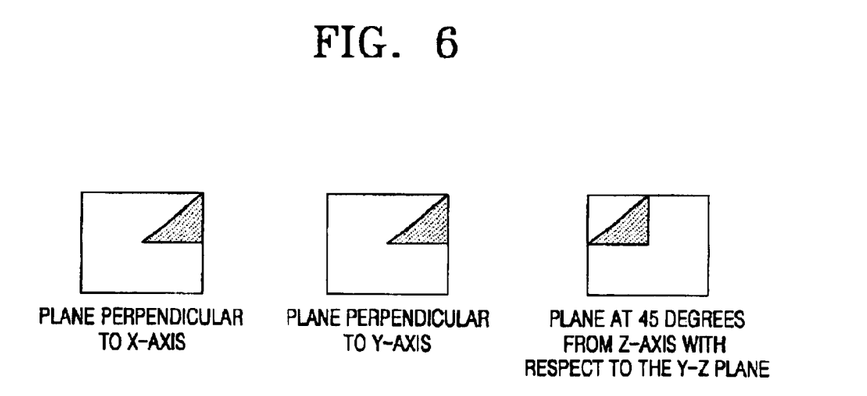
FIG. 6 shows overlapped portions of data acquired using the three sensors, according to the present invention.

FIG. 6 shows the overlapped areas of the parts sensed and extracted from the three sensors according to the present invention. To form a three-dimensional structure as shown in FIG. 5, ⅛ of the part which the sensor 202 on the X-axis direction senses, ⅛ of the part which the sensor 204 on the Y-axis direction senses, and ⅛ of the part which the sensor 206 on the plane making a 45 degrees from the Z-axis with the Y-Z plane senses are overlapped.

Accordingly, three-dimensional data extraction is performed by matching the overlapped portions to each other and finding corresponding points. This method is more accurate than the conventional method extracting three-dimensional data from two sets of data. When three matching points are found, a three-dimensional location of a point in space can be determined according to the operation determining a disparity in the disparity determination unit 210.

If it is assumed that a disparity between two points is $Z_1$, a distance $\Delta Z_p$ between practical depths of the two points is obtained as follows. In a parallel optical axis, if $\Delta Z_p$ is the distance between the practical depths when the disparity value is 1 on a horizontal line in a current resolution, a distance from a camera to an object is determined by Equation 2 below.

$$\Delta Z_P = \frac{2Z_1^2 \tan\phi}{Nb - 2Z_1 \tan\phi} = \frac{Z_1^2}{fb\Delta P - Z_1} \quad (2)$$

Wherein b denotes the distance from the camera to the object, $\phi$ denotes an angle of the camera with respect to the object, $\Delta P$ is equal to $$\frac{N}{2f \tan\theta},$$

and N denotes the number of pixels in the width directions on the image.

It is found by the above Equation 2 that in the parallel optical axis, a depth resolution becomes greater, as the baseline distance and focusing distance are greater and also as the distances from the sensors to the object are smaller.

If the baseline is extended or the object is moved near to the camera in order to enhance the depth resolution, probability of mismatching is increased. That is, a tradeoff exists between the accuracy of matching and the density of resolution of disparity rate. Accordingly, by using the three sensors, depth information having high resolution can be extracted and simultaneously the accuracy of matching can be enhanced.

For efficient matching, it is necessary to compensate data acquired using the three sensors. Since an electron microscope has high resolution, the overlapped area becomes smaller. Accordingly, there are often situations where the occlusion area of the object is increased, and disparity information is lost around the boundary of the object. To widen the overlapped area, it is desired to use the same epipolar line for all three sensors.

Hereinafter, a method for obtaining matching pixel count-multiple baseline stereo (MPC-MBS) in three pictures including two-dimensional coordinates extracted from the three sensors by the disparity determination unit 210 will be described.

For example, for obtaining a model of a human face, a camera having a predetermined depth resolution should be provided. The MPC-MBS matching method according to the present invention is provided to prevent accuracy of matching from being deteriorated. In the present invention, since depth information having high resolution is required, the baseline distance values of the sensors is greater so that the accuracy of matching is not deteriorated.

Conventional matching methods for measuring a similarity include SAD (Sum of Absolute Distance), SSD (Sum of Squared Distance), NCC (Normalized Correlation Coefficient), etc. In such conventional similarity measurement methods, since one pixel in a matching window affects similarity depending on the brightness value of the pixel, a boundary overreach, i.e., a situation where a boundary line of disparities is extended from an area having a greater brightness variation among pixels to an area having a smaller brightness variation among pixels, is generated, thereby an erroneous result in the boundary portion occurs.

The method for obtaining the three-dimensional depth information according to the present invention is based on the method "A High Performance Disparity Information Extraction Algorithm using low Resolution Disparity Histogram," by Nam-Gyu Kim, Kwang-Do Lee, Heong-Gon Kim, and Gyun-Hyun Cha, The Institute of Electronics Engineering of Korea (IEEK), Vol.3, No.3, pp.131–143, March 1998.

According to an MPC matching method, it is possible to obtain a good result even on the boundary portion by making each pixel having the same influence on similarity regardless of the brightness values of pixels.

If it is assumed that $W_r$ and $W_c$ represent the vertical and horizontal lengths of a matching window, respectively, and $w_r$ and $w_c$ represent the vertical and horizontal distances of the window from the center of the window respectively, an MPC similarity between a pixel in a base image having a location (x,y) and a pixel in a searched image spaced a disparity d is determined according to Equation 3 below.

$$w_r = \frac{W_r - 1}{2}, \; w_c = \frac{W_c - 1}{2} \quad (3)$$

$$MPC(x, y, d) = \sum_{i=x-w_c}^{x+w_c} \sum_{j=y-w_r}^{y+w_r} T(i, j, d) = \sum_{W} T(x, y, d)$$

$$T(x, y, d) = \begin{cases} 1, & \text{if } |R_{x,y} - L_{x+d,y}| \leq Th \\ 0, & \text{otherwise} \end{cases}$$

wherein, W denotes the size of the window, and $R_{x,y}$ and $L_{x,y}$ denotes the brightness values of the pixels at the location (x,y) on the left and right images respectively. Here, T(x,y,d) is 1 if the brightness values of pixels at a location (x,y:x+d,y) are similar and is 0 if the brightness values are not similar. Th is a predetermined threshold value. A disparity D(x,y) at location (x,y) is determined by maximizing MPC(x,y,d) with respect to d as shown in Equation 4.

$$D(x,y) = \text{argmax}_d MPC(x,y,d) \quad (4)$$

In the MPC-MBS matching method, the searched images are both left and right images of the base image, wherein a similarity value is determined by the sum of a MPC value at a point (x,y) of the searched left image and a MPC value at the point (x,y) of the searched right image. MPC-MBS between a pixel located at the point (x,y) on the base image and a pixel on the searched image spaced by a disparity d is determined by Equation 5 below.

$$MPC\_MBS = MPC_L + MPC_R \quad (5)$$

$$MPC_L = \sum_W T_L(x, y, d), \; MPC_R = \sum_W T_R(x, y, d)$$

$$T_L(x, y, d) = \begin{cases} 1, & \text{if } |M_{x,y} - L_{x+d,y}| \leq Th \\ 0, & \text{otherwise} \end{cases}$$

$$T_R(x, y, d) = \begin{cases} 1, & \text{if } |M_{x,y} - R_{x-d,y}| \leq Th \\ 0, & \text{otherwise} \end{cases}$$

wherein $M_{x,y}$, $R_{x,y}$, and $L_{x,y}$ denote the brightness values at the location (x,y) on the middle, right and left images, respectively.

The disparity D(x,y) at the point (x,y) on the base image is determined by Equation 6 below.

$$D(x,y) = \text{argmax}_d MPC\_MBS(x,y,d) \quad (6)$$

The three-dimensional data extraction unit 220 extracts three-dimensional depth information of an object, representing a relative distance to the object, using the obtained disparity, and extracts three-dimensional coordinates of each pixel to determine a three-dimensional location of the object (step 120).

At this time, it is desired to prevent the computational time from being increasing with the size of the matching window by removing double operations in obtaining MPC-MBS.

It is assumed that the resolution of the image is ($I_r \times I_c$), the size of the matching window is ($W_r \times W_c$) and the searching range is $S_r$, (N−1)×($I_r \times I_c$)×($W_r \times W_c$)×$S_r$ can reduced to (N−1)×($I_r \times I_c$)×$S_r$.

Since only three images are used according to the present invention, the value of N is 3. It is assumed that V represents matching of the horizontal lines corresponding to the height W of the matching window, and MPC represents matching window block between the windows, the MPC-MBS operation method in which the double operations are removed is represented as follows.

First, a double operation removal of the base image and the left image is performed using Equation 7. The computational time is not influenced by the size of the matching window and is in proportion to (N−1)×($I_r \times I_c$)×$S_r$. If it is assumed that $S_r$ denotes the searching area, N denotes the number of images and $W_r$ and $W_c$ denote the sizes of the matching windows in the MPC-MBS matching, the total operation amount of the MPC-MBS matching is determined by the following Equation 7.

$$V_L(x, y, d) = \sum_{j=y-W_r}^{y+W_r} T_L(x, j, d) \quad (7)$$

$$V_L(x, y+1, d) = V_L(x, y, d) + T_L(x, y+1+W_r, d) - T_L(x, y-W_r, d)$$

$$MPC_L(x+1, y, d) = MPC_L(x, y, d) + V_L(x+1+W_c, y, d) - V_L(x-W_c, y, d)$$

Likewise, a double operation removal between the base image and the right image is performed using Equation 8.

$$V_R(x,y+1,d)=V_R(x,y,d)+T_R(x,y+1+W_r,d)-T_R(x,y-W_r,d) \; MPC_R(x+1,y,d)=MPC_R(x,y,d)+V_R(x+1+W_c,y,d)-V_R(x-W_c,y,d) \quad (8)$$

Types of the double operations that occur upon matching include a block double operation generated whenever the matching window is moved by one pixel and a horizontal-line double operation generated when the matching window is moved horizontally. The block double operation and the horizontal-line double operation are removable using Equations 9 and 10 below.

When the three-dimensional data extraction unit 220 extracts the three-dimensional depth information of the object, representing the relative distance of the object, using the obtained disparity, and extracts the three-dimensional coordinates on each pixel to determine the three-dimensional location of the object, once the disparity is obtained, it is desired to obtain disparities having continuity by approximating the disparity as a quadratic function on the basis of a pixel having maximum similarity and interpolating the disparity using a pole point thereof as a corresponding point.

The quadratic function formula used for improving disparity rate is given by Equation 9.

$$y = ax^2 + bx + c \quad (9)$$

If is assumed that the pixel at the location (x,y) has maximum similarity $M_{x,y}(d_{max})$, Equation 9 is approximated to the peripheral values of $d_{max}$. This can be represented as shown in Equation 10 below.

$$Ax = b \quad (10)$$

$$\text{wherein, } A = \begin{bmatrix} (d_{max}-1)^2 & (d_{max}-1) & 1 \\ d_{max}^2 & d_{max} & 1 \\ (d_{max}+1)^2 & (d_{max}+1) & 1 \end{bmatrix}$$

$$x = \begin{bmatrix} a \\ b \\ c \end{bmatrix}, \quad b = \begin{bmatrix} M_{x,y}(d_{max}-1) \\ M_{x,y}(d_{max}) \\ M_{x,y}(d_{max}+1) \end{bmatrix}$$

wherein x is determined using a pseudo-inverse method as in Equation 11 below.

$$x = (A^T A)^{-1} A^T b \quad (11)$$

In the above quadratic function, since $$-\frac{b}{2a}$$

is an exact pole point of the quadratic function, it can be considered as a disparity value having decimal point accuracy. In this way, the surface depth information quantized using the depth resolution of Equation 2 by enhancing the resolution of the disparity rate to decimal point pixel unit is made more smoothly.

Three-dimensional parameters often provide more correlation than the two-dimensional parameters. Examples of the three-dimensional parameters used in the present invention are described below.

1. $S_q$ (Root-mean-Square Deviation)

It is a dispersion value within a given section and frequently used as a three-dimensional parameter. Also, it is not sensitive to distances between the sections, but is very sensitive to sizes of the sections.

$$S_q = \sqrt{\frac{1}{MN}\sum_{j=1}^{N}\sum_{i=1}^{M}\eta^2(x_i, y_j)} \quad (12)$$

wherein $\eta(x_i,y_j)$ is a height at a point ($x_i, y_j$).

2. $S_q$ (Ten points Height of the Surface)

This parameter corresponds to $R_z$ (surface irregularity rate) in 2D and is a value obtained by extending the section to 3D. When the section is a rectangular area of dimensions X and Y, $S_z$ is determined as below.

$$S_z = \frac{\sum_{i=1}^{5}|\eta_{\pi}| + \sum_{i=1}^{5}|\eta_{vi}|}{5} \quad (13)$$

3. $S_{sk}$ (Skewness of Surface Height Distribution)

This parameter is very useful for representing curved aspects for three-dimensional surface.

$$S_{sk} = \frac{1}{MNS_q^3}\sum_{j=1}^{N}\sum_{I=1}^{M}\eta^3(x_i, y_j) \quad (14)$$

4. TSa (Three dimensional Surface Area)

A distance between two points P1 (X1,Y1,Z1) and P2(X2, Y2,Z2) in a three-dimensional space is $$\sqrt{(X2-X1)^2 + (Y2-Y1)^2 + (Z2-Z1)^2}.$$

On the basis of this value, if three points in the three-dimensional space are (0,0,a), (0,1,a) and (1,0,b), distances s1, s2 and s3 among the respective points are $1+(a-b)^2$, $1+(a-c)^2$, and $2+(b-c)^2$ respectively. At this time, the area value of a triangle having the three points as vertexes thereof is $$\sqrt{S \cdot (S-s1)(S-s2)(S-s3)},$$

wherein S=(s1+s2+s3)/2. Accordingly, the surface area of the whole section becomes the sum of the triangle areas obtained using the coordinates of the three points when all x and y are changed respectively by 1.

5. TV (Three Dimensional Volume)

This value is the sum of all volumes over a base plane and all volumes under the base plane. That is, the volume over the base plane is determined by $$\int_y \int_y z = \int_y \int_y f(x, y),$$

wherein x and y points are provided respectively as a predetermined interval (here, 1) within a given extent, and z value also is an integral value. Accordingly, the volume is determined by the sum of two triangular columns having a height of $Z_c$ within the area in which x and y values are 1. When the locations of the three points are (0,0,1), (1,0,b) and (0,1,c), the volume is calculated using the following Equation 15. The Equation of a plane determined by the three points (0,0,1), (1,0,b), and (0,1,c) is (a-b)x+(a-c)y+z=a, wherein $0 \leq x \leq 1$, $0 \leq y \leq -x+1$. Therefore, the volume is obtained as follows:

$$V = \int_0^1 \int_0^{-x+1} (a - (a-b)x - (a-c)y)\,dy\,dx \qquad (15)$$
$$= \int_0^1 (\frac{a+c}{2} - (a-b+c)x + \frac{a-2b+c}{2}x^2)$$
$$= \frac{(a+b+c)}{6}$$

While the present invention has been particularly shown and described with reference to exemplary embodiments thereof, it will be understood by those of ordinary skill in the art that various changes in form and details may be made therein without departing from the spirit and scope of the present invention as defined by the following claims.

The steps of the present invention can be implemented as a computer readable code in a computer readable medium. The computer readable medium includes all sorts of recording devices for storing data capable of being read by a computer system. The invention may be embodied in a general purpose digital computer by running a program from a computer readable medium, including but not limited to storage media such as magnetic storage media (e.g. ROM's floppy disks, hard disks, etc.), optically readable media (e.g. CD-ROMs, DVDs, etc.) and carrier waves (e.g. transmissions over the Internet). Also, the present invention may be embodied on a computer readable medium having a computer readable program code unit therein to be executed in a computer network.

Therefore, according to the present invention, it is possible to three-dimensionally analyze even minor objects observed through an electron microscope, by obtaining two-dimensional coordinates by respectively projecting the object on a plane perpendicular to an X-axis, on a plane perpendicular to a Y-axis, and on a plane making an angle of 45 degrees from a Z-axis with a Y-Z plane, in an XYZ coordinate system; in portions where three images including the two-dimensional coordinates overlapped, obtaining data of a pixel on a base images among the three images, obtaining data of corresponding pixels of the pixel on the base image to left and right images of the base image, and calculating a disparity on the basis of the data; and extracting three-dimensional depth information of the object using the obtained disparity, the three-dimensional depth information representing a relative distance of the object, and extracting a three-dimensional coordinate on each pixel to determine a three-dimensional location of the object, thereby providing an important tool for the research of cells and various diseases, which can be also used in the precision industry.

Three-dimensional cognition of the inside of cells or the organizations or minor structures thereof is essential to understanding cell functions. A conventional technique in this respect is to three-dimensionally construct images of successive sections via an optical microscope or transmission electron microscope. However, the conventional technique has difficulties obtaining these samples and observing them. It may also result to many errors in the analysis.

The purpose of directly measuring the lengths, diameters, and angles of structures existing on cell surfaces, and the sizes and correlation of organellas while directly observing three-dimensional images through a microscope is to ultimately understand the cell functions. However, constructing a three-dimensional structure with the conventional scanning electron microscope is merely a method for converting an existing scanning electron microscope data into a three-dimensional structure using a computer.

However, the scanning electron microscope having high accuracy according to the present invention can contribute to the development of precision equipment. Particularly, since the three-dimensional scanning microscope according to the present invention is absolutely new, the present invention can have a tremendous effect in related industries such as semiconductor manufacturing.

Also, it is possible to obtain a very precise diagnosis using the electron microscope of the present invention when treating cell surface variances, and to contribute to the development of the related art by understanding minor structural variances based on 3D data of cells, which is essential in various medical researches.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A screen, comprising:
    a projection surface on which a light beam irradiated by an optical equipment is projected to form a projection image;
    a luminous energy sensor provided on the projection surface, the luminous energy sensor detecting a luminous energy of the light beam irradiated by the optical equipment; and
    an attitude controller that controls the attitude of the projection surface facing the optical equipment based on the luminous energy detected by the luminous energy sensor.

2. The screen according to claim 1, further comprising:
    a first drive mechanism that turns the projection surface around a first axis extending along a horizontal direction of the projection surface; and
    a second drive mechanism that turns the projection surface around a second axis extending in a vertical direction of the projection surface, the attitude controller controlling the first drive mechanism and the second drive mechanism.

3. The screen according to claim 2, the luminous energy sensor including four photoelectric transducers including a first pair of photoelectric transducers and a second pair of photoelectric transducers, the first pair of photoelectric transducers being provided along the vertical direction of the projection surface and the second pair of photoelectric transducers being provided along the horizontal direction of the projection surface.

4. The screen according to claim 3, the photoelectric transducer being a photodiode.

5. The screen according to claim 3, the luminous energy sensor having a bridge circuit that uses the four photoelectric transducers as resistor elements.

6. The screen according to claim 4, the luminous energy sensor having a bridge circuit that uses the four photoelectric transducers as resistor elements.

7. The method of claim 3, wherein in determining the three-dimensional location of the object, once the disparity is obtained, the disparities have continuity by approximating matching pixel count_multiple baseline stereo (MPC-MBS) as a quadratic function on the basis of a pixel having maximal similarity and interpolating the disparity using a pole point thereof as a corresponding point.

8. The method of claim 4, wherein in determining the three-dimensional location of the object, once obtaining the disparity, the disparities have continuity by approximating matching pixel count_multiple baseline stereo (MPC-MBS) as a quadratic function on the basis of a pixel having a maximal similarity and interpolating the disparity using a pole point thereof as a corresponding point.

9. An apparatus for extracting three-dimensional data of an object using an electron microscope, the apparatus comprising:

sensors which sense two-dimensional coordinates obtained by respectively projecting the object respectively on a plane perpendicular to an X-axis, a plane perpendicular to a Y-axis, and a plane making an angle of 45 degrees from a Z-axis with a Y-Z plane;

a disparity determination unit which, in respective overlapped portions of three images including the two-dimensional coordinates respectively sensed by the sensors, obtains data of corresponding pixels of a pixel on a base image to left and right images of the base image, and calculates a disparity on the basis of the data; and three-dimensional data extraction unit which extracts three-dimensional depth information of the object using the disparity determined by the disparity determination unit, the three-dimensional depth information representing a relative distance of the object, and extracts a three-dimensional coordinate on each pixel to determine a three-dimensional location of the object.

10. The apparatus of claim 9, wherein in the disparity determination unit, matching pixel count (MPC) of a pixel having a location (x,y) on a base image and a pixel on a searched image spaced by a disparity d from the base image is determined by the following equations:

$$wr = \frac{W_r - 1}{2}, wc = \frac{W_c - 1}{2}$$

$$MPC(x, y, d) = \sum_{i=x-w_c}^{x+w_c} \sum_{j=y-w_r}^{y+w_r} T(i, j, d) = \sum_W T(x, y, d)$$

-continued $$T(x, y, d) = \begin{cases} 1, & \text{if } |R_{x,y} - L_{x+d,y}| \leq Th \\ 0, & \text{otherwise} \end{cases},$$

wherein $W_r$ and $W_c$ are the vertical and horizontal lengths of a matching window respectively, $w_r$ and $w_c$ are the vertical and horizontal lengths of the window from the center of the window respectively, W is the size of the window, $R_{x,y}$ and $L_{x,y}$ are the brightness values of the pixels at the location (x,y) on the left and right images respectively, Th is a predetermined threshold value, and a disparity D(x,y) at the location (x,y) is determined by D(x,y)=argmax$_d$MPC(x,y,d), wherein d denotes an value where MPC(x, y, d) value is maximum.

11. The apparatus of claim 10, wherein in the disparity determination unit, the searched images are the left and right images of the base image and the similarity value is determined by the sum of respective MPC values of the searched left image and the searched right image of the point (x,y), MPC of the pixel at the location (x,y) on the base image and the pixel on the searched image spaced by the disparity d from the base image is determined by the following equations:

$$MPC\_MBS = MPC_L + MPC_R$$

$$MPC_L = \sum_W T_L(x, y, d), MPC_R = \sum_W T_R(x, y, d)$$

$$T_L(x, y, d) = \begin{cases} 1, & \text{if } |M_{x,y} - L_{x+d,y}| \leq Th \\ 0, & \text{otherwise} \end{cases}$$

$$T_R(x, y, d) = \begin{cases} 1, & \text{if } |M_{x,y} - R_{x-d,y}| \leq Th \\ 0, & \text{otherwise} \end{cases},$$

wherein $M_{x,y}$, $R_{x,y}$, and $L_{x,y}$ are the brightness values of the pixels at the location (x,y) on the center, right and left images of the base image respectively, and the disparity D(x,y) at the pixel (x,y) on the base image is determined by D(x,y)=argmax$_d$MPC_MBS(x,y,d).

12. The apparatus of claim 10, wherein in the three-dimensional data extraction unit, double operations are removed by not performing operations for overlapped portions among vertical lines when the window is moved for image matching with overlapped areas of the left or right image and the base image, according to a predetermined method.

13. The apparatus of claim 11, wherein in the three-dimensional data extraction unit, double operations are removed by not performing operations for overlapped portions among vertical lines when the window is moved for image matching with overlapped areas of the left or right image and the base image, according to a predetermined method.

14. The apparatus of claim 10, wherein in the three-dimensional data extraction unit, once the disparity is obtained, the disparities have continuity by approximating matching pixel count_multiple baseline stereo (MPC-MBS) as a quadratic function on the basis of the pixel having maximal similarity and interpolating the disparity using a pole point thereof as a corresponding point.

15. The apparatus of claim 11, wherein in the three-dimensional data extraction unit, once the disparity is obtained, the disparities have continuity by approximating matching pixel count_multiple baseline stereo (MPC-MBS) as a quadratic function on the basis of the pixel having maximal similarity and interpolating the disparity using a pole point thereof as a corresponding point.

* * * * *